United States Patent [19]

Gaffar et al.

[11] Patent Number: 4,843,099

[45] Date of Patent: Jun. 27, 1989

[54] DEVICE AND COMPOSITION FOR TREATMENT OF THE GUMS

[75] Inventors: Abdul Gaffar, Princeton; John Afflitto, Brookside, both of N.J.

[73] Assignee: Colgate-Palmolive Company, New York, N.Y.

[21] Appl. No.: 75,165

[22] Filed: Jul. 20, 1987

[51] Int. Cl.$^4$ .................. A61K 31/185; A61K 9/08
[52] U.S. Cl. ..................................... 514/576; 128/66
[58] Field of Search ........................ 128/66; 514/576

[56] References Cited

U.S. PATENT DOCUMENTS

| | | | |
|---|---|---|---|
| 4,185,100 | 1/1980 | Rovee et al. | 514/171 |
| 4,360,518 | 11/1982 | Rovee et al. | 514/887 |
| 4,473,565 | 9/1984 | Rovee et al. | 514/174 |
| 4,496,589 | 1/1985 | De Vincentis | 514/565 |
| 4,569,837 | 2/1986 | Suzuki et al. | 514/781 |
| 4,579,844 | 4/1986 | Rovee et al. | 514/171 |
| 4,599,359 | 7/1986 | Cooper | 514/557 |
| 4,617,918 | 10/1986 | Donohue et al. | 128/66 |
| 4,647,453 | 3/1987 | Meisner | 424/54 |
| 4,681,544 | 7/1987 | Anthony | 433/215 |
| 4,704,406 | 11/1987 | Stanislaus et al. | 514/576 |
| 4,772,470 | 9/1988 | Inoue et al. | 424/435 |
| 4,772,591 | 9/1988 | Meisner | 514/474 |
| 4,780,320 | 10/1988 | Baker | 424/493 |

FOREIGN PATENT DOCUMENTS 900481 2/1985 Belgium .

OTHER PUBLICATIONS

Topical Fluorobiprogen Treatment of Periodontitis in Beagles, Williams et al, Journal of Periodontal Research 1988, vol. 23, pp. 166–169.

Wechner CA. 102: 226058m (1985) of Borg. BE 900481, 1985.

Rosenthale Ca. 96: 738d (1982).

*Primary Examiner*—Shep K. Rose
*Attorney, Agent, or Firm*—Robert L. Stone; Murray M. Grill

[57] ABSTRACT

Ibuprofen, pharmaceutically acceptable salt thereof or lower alkyl $C_{1-6}$ ester thereof, in solution in periodontal gum device comprising elongated handle member terminating proximally in a flexible tip portion provided with an aperture for discharge of the solution which is effective to reduce gingival inflammation and swelling.

3 Claims, 3 Drawing Sheets

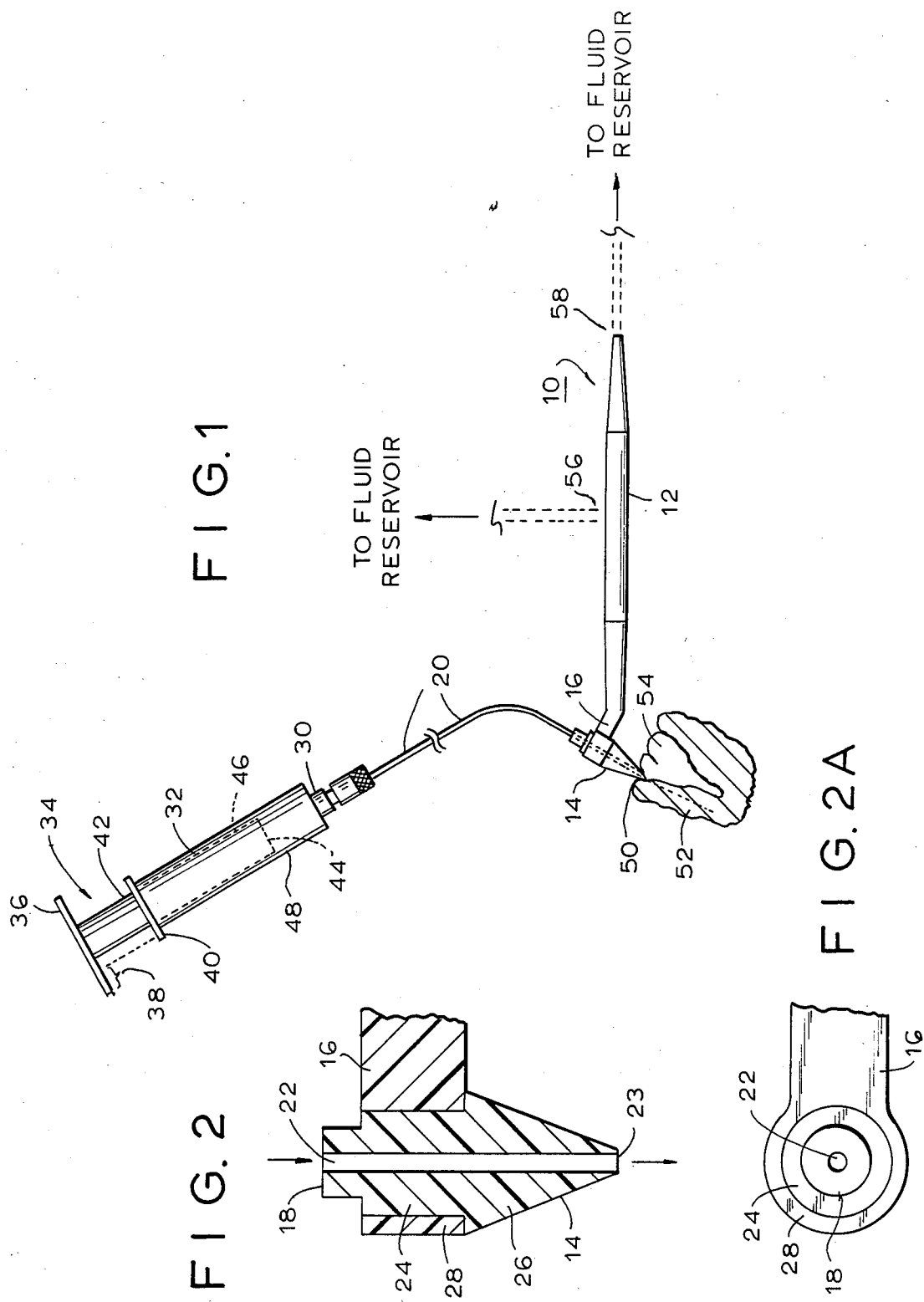

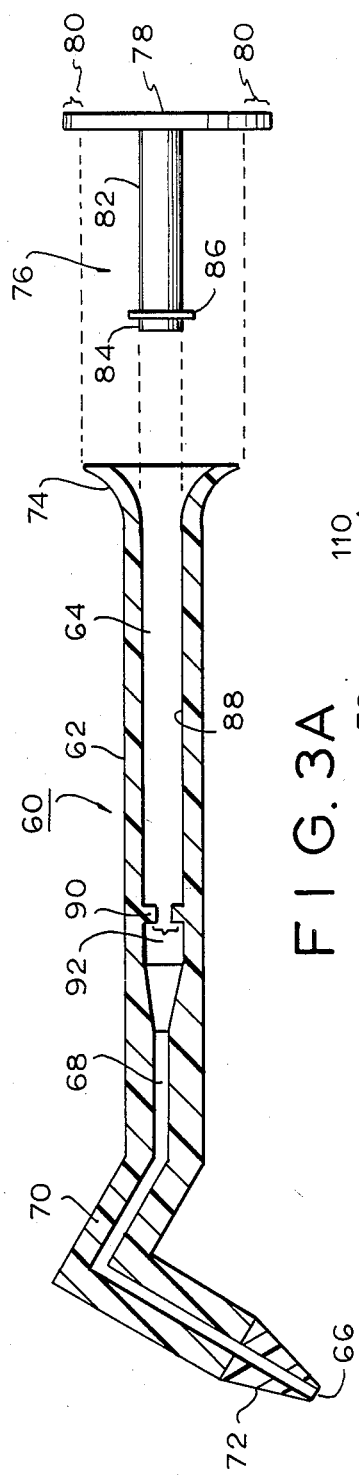
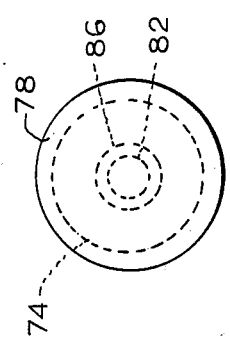
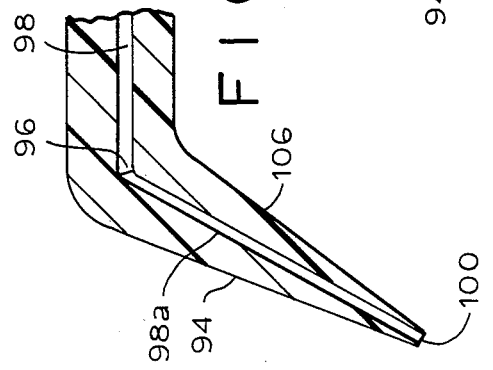
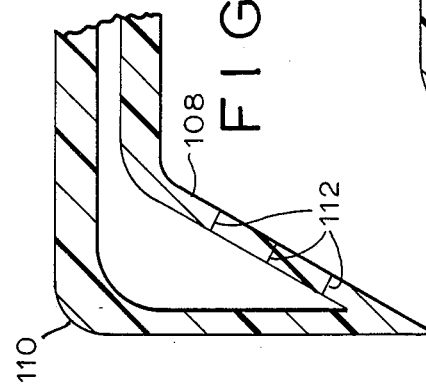
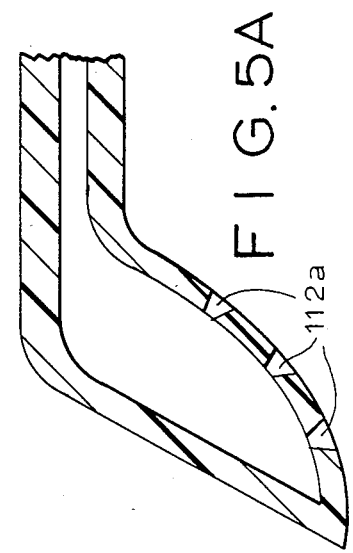

DEVICE AND COMPOSITION FOR TREATMENT OF THE GUMS

This invention relates to improving the hygiene of the gums by applying an anti-inflammatory composition directly into pockets into the gingival sulcus from a device configured to manipulate the gingival sulcus.

It has been taught in the art to incorporate into topically applied oral compositions, such as dental creams and mouth rinses, materials which promote oral hygiene and reduce gingivitis. For instance, U.S. Pat. Nos. 4,272,512; 4,272,513; and 4,309,410; each to Gaffar, disclose oral compositions containing tranexamic acid antigingivitis agent.

In U.S. Pat. No. 4,617,918 to Donohue et al, a device is described of the type which may be employed in accordance with the present invention. The device has a tip configured to expedite probing contact with the gingival sulcus and an aperture through which liquid from a reservoir is supplied for discharge into subgingival areas. The liquid supplied may be irrigant such as an isotonic saline solution and/or a medicament liquid.

In Belgian Pat. No. 900,481 to Upjohn, Ibuprofen and flurbiprofen are disclosed as materials which prevent or inhibit resorption of alveolar bone in warm blooded animals when administered orally, topically or bucally or by injection or subdermal immplantation. One of the most common peridontal conditions in chronic destructive periodontitis resulting in progressive loss of alveolar bone leading to tooth mobility and loss. This condition, chronic distructive periodontis, which is prevented by inhibited by Ibroprofen or flurbirofen, is distinguished from the other common periodontal condition, chronic gingivitis, wherein the gingiva are inflamed.

Ibuprofen and flurbiprofen are anti-inflammatory compounds. Indeed, in addition to its effect in reducing alveolar bone resorption, it has been observed that flurbiprofen also appears to reduce gingival inflammation and swelling upon topical application. However, Ibuprofen, the alternate inhibitor of bone resorption in Belgian Pat. No. 900,481 when incorporated into mouth rinse is observed to be without effect in reducing gingival inflammation and swelling.

It is an advantage of this invention that the anti-inflammatory properties of Ibuprofen are employed to reducing gingival inflammation and swelling.

It is a further advantage of this invention that a periodontal gum device is employed to effectuate the anti-inflammatory property of Ibuprofen against inflammation and swelling.

Further advantages of this invention will be apparent from consideration of the following specification.

In accordance with certain of its aspects, this invention relates to a periodontal gum device comprising an elongated handle member terminating proximally in a flexible tip portion provided with at least one aperture for discharge of a solution containing 0.1-5% by weight of Ibuprofen, a pharmaceutically acceptable salt thereof or lower alkyl $C_{1-6}$ ester thereof, which is stored in a fluid reservoir in said device from which said solution is delivered to said aperture, said tip portion being configured to expedite probing contact with gingival sulcus and permit discharge of said solution into gingival sulcus.

Ibuprofen is α-methyl-4-(2-methylpropyl)benzeneacetic acid and is prepared as described in U.S. Pat. No. 3,228,831. Its structure is:

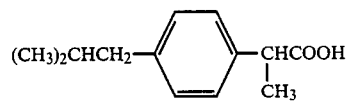

In addition to Ibuprofen itself, as the active material ester of Ibuprofen for the inhibition or prevention of gingival inflammation and swelling. Pharmaceutically acceptable salts of Ibuprofen useful in practicing the present invention are alkali metal salts such as the potassium or sodium salt, alkaline earth salts such as calcium or magnesium, or amine salts such as t-butyl amine. Lower alkyl $C_{1-6}$ esters of Ibroprofen useful in practicing the present invention include the methyl, ethyl, n-propyl, isopropyl, n-butyl, isobutyl, t-butyl, pentyl and hexyl ester. Such compounds are essentially as set forth in Belgian Pat. No. 900,481. Ibuprofen is present in the fluid reservoir in amount of about 0.1-5% by weight, preferably about 1-3%, in water and/or humectant such as glycerine, sorbitol syrup, polyethylene glycol 400 or 600 and/or essential oil such as oil of cloves, peppermint, spearmint or wintergreen (methyl salicylate). A surface active agent such as an anionic surfactant (e.g. sodium lauryl sulfate), a non-ionic surfactant (e.g. a Pluronic material) or a cationic surfactant (e.g. betaine) may also be present in amount of about 0.1-5% by weight. A preservative such as sodium benzoate may be present. The pH may be adjusted, typically between about 7-8.5. A typical periodontal gum device useful to convey Ibuprofen solution to gingival packets is as described in U.S. Pat. No. 4,617,918. A design modification of the device is described in co-pending, commonly assigned, U.S. patent application Ser. No. 61984 filed June 8, 1987. It is further described in detail by reference to the accompanying drawings wherein like reference numerals designate similar parts throughout the views and wherein:

BRIEF DESCRIPTION OF THE DRAWINGS

FIG. 1 schematically illustrates embodiments of the device wherein the fluid reservoir portion comprises a physically separate member;

FIG. 2 is a vertical sectional view of the tip portion of FIG. 1;

FIG. 2a is a top view (shown in full) of the tip portion of FIG. 2;

FIG. 3 is a side view taken in section illustrating an additional embodiment of the device;

FIG. 3a is a top view of an insert cap in accordance with the device;

FIGS. 4 and 4a illustrate in vertical section, shown partly broken away, a value actuated tip portion in accordance with the device;

FIGS. 5 and 5a illustrate in vertical section, shown partly broken away, a valve actuated tip portion in accordance with an additional embodiment of the device.

DETAILED DESCRIPTION OF THE DEVICE

Figure 6:
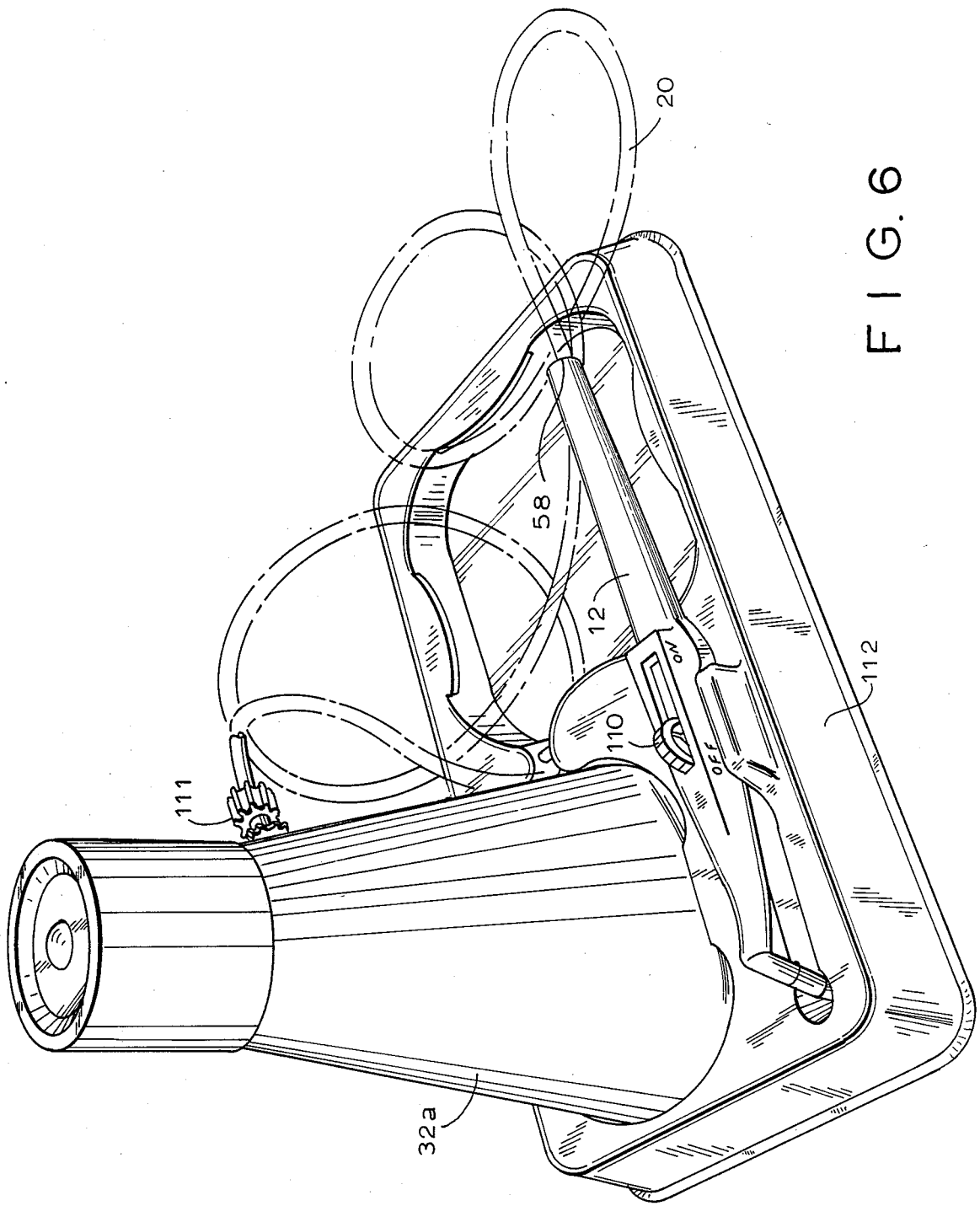
FIG. 6 illustrates a modification of the device of FIG. 1.

The device as illustrated schematically in the embodiment of FIG. 1 comprises an elongated probe element indicated generally at 10 comprising a handle member 12 which may be solid or tubular construction as will be explained and may be circular, rectilinear, etc., in cross section to expedite hand gripping. The probe 10 terminates proximally in a flexible tip portion 14 through a neck portion 16, angled as illustrated to facilitate positional maneuvering of the tip portion 14 within the oral cavity. As illustrated in FIGS. 2 and 2a, the tip portion 14 consists of a cylindrical neck portion 18 for fixedly receiving a conduit 20 to a depth within a channel 22 as is consistent with structural integrity. Attachment may be secured by adhesive or other suitable means, as is known. Stepped cylindrical portions 24 and 26 provide a configuration consistent with structured stability and avoid corner portions which might otherwise be injurious to the gum during use of the device. The tip portion 14 is secured to the handle member 12 via a ring portion 28 integral with the neck 16. The tip 14 converges downwardly as illustrated at 26, terminating at the outer end 23 of the channel. The conduit 20 connects the tip portion 14 with the outlet port 30 of fluid reservoir 32 containing Ibuprofen, the latter as illustrated in FIG. 1 being a component physically separate from the probe 10 and generally comprising a syringe type device of cylindrical cross section. A removable cap insert 34 comprises lid 36 having a diameter greater than that of the tip 40 of the reservoir 32 thus providing a peripheral portion 38 for facilitating hand removal of the cap 34, as for example, when recharging the reservoir 32. The sidewall 42 of the cap 34 is provided at its leading or lower edge portion 44 with a washer 46 sized to functionally engage at its outer vertical edge the inner surface of the sidewall 48 of the Ibuprofen solution reservoir 32 thereby hermetically sealing the fluid contents of the reservoir.

Use of the FIG. 1 device is as follows: Ibuprofen solution is charged to the fluid reservoir 32 and the cap 34 is positioned as illustrated. The diameters of the conduit 20 and the channel 22, and particularly the latter, are relatively small, to the extent that flow of charged fluid through the channel 22 is prevented principally by virtue of fluid surface tension effects unless and until the requisite pressure is applied causing downward displacement of the cap 34 along its longitudinal axis. The probe 10 is positioned in the oral cavity so that the other end of the channel portion of the tip 14 is inserted into the gingival sulcus indicated at 50 in FIG. 1; i.e., the space between the gum 52 and the tooth 54, also referred to as the tooth socket. The locus thus having been determined, the user forcibly depresses the cap 34; the application of relatively slight pressure suffices to overcome the aforementioned flow resistance thereby resulting in the discharge of Ibuprofen solution through the channel 22 to the determined area. In this manner, Ibuprofen is delivered at a point below the gum line, that is subgingivally.

In further embodiments, the conduit 20 may be attached to the handle member 12 at points 56 or 58 respectively as indicated by the phantom lines in FIG. 1. In such cases, the handle 12 is of tubular construction to establish a continuous flow path between the fluid point of entry and the channel 22. Distal end connection as indicated at 58 is preferably being less likely to obstruct the user's gripping or manipulation of the device.

The device may be used to the point of substantially complete exhaustion of the solution. As will be apparent, air present in the reservoir 32 provides a cushion sufficient to enable the cap 34 to function as a piston despite the total absence of fluid in the reservoir. In any event, the ratio of the total volume of reservoir to total volume of conduit is usually quate large and thus waste due to unused conduit fluid is insigificant.

Manipulation of the FIG. 1 device by the user requires both hands as opposed to the FIG. 3 device requiring but one hand. In the latter device generally designated 60 the handle 62 is of tubular construction the distal end portion thereof serving as the Ibuprofen solution reservoir 64. The latter is in fluid flow communication with the aperture 66 via the conduit 68 proceeding through the neck portion 70, angled as previously described, and then through the tip portion 72 convergent downwardly terminating in the aperture 66. The diameter of the reservoir 64 is relatively large compared to that of the conduit 68 for the reasons previously described as well as to practically limit the length of the device. The handle 62 terminates distally in an outwardly flared or trumpeted portion 74 providing a funnel type end to facilitate charging of Ibuprofen solution to the reservoir 64. The insert cap 76 is similar in configuration to the cap 34 of FIG. 1 comprising a lid 78 having a diameter greater than dotted lines in FIGS. 3 and 3a thus providing a gripping area 80 for removal of the cap 76 from the fully closed (inserted) position. The sidewall 82 is provided at its leading or lower end portion 84 with a washer 86 having a vertical edge adapted upon insertion to functionally engage the inner surface 88 of the handle 62 to thereby hermetically seal the Ibuprofen solution in the reservoir 64 and to stabilize the position of the cap 76.

The FIG. 3 device is used as follows: Ibuprofen solution is charged to the reservoir 64 in the amount desired. In the absence of pressure, fluid flow through the aperture 66 does not occur due to surface tension effects as described. The cap 76 is inserted into the reservoir 64 to a depth penetration sufficient to stabilize its placement. Some albeit minor solution flow through the aperture 66 may occur indicating the attainment of solution discharge pressure. The device is positioned in the oral cavity in the manner previously described using the thumb or forefinger of the gripping hand to depress the cap 76 to initiate and sustain fluid discharge through the aperture 66.

In a further embodiment, the reservoir 64 may be charged with a rupturable packet, cartridge or other suitable container encasing the Ibuprofen solution under pressure. The packet, configured in accordance with the internal dimensions of the reservoir 64 so as to snugly fit therewith, is inserted into the reservoir so as to engage abutting means provided therin such as the annular flange 90 (FIG. 3) integrated with the handle 62 and defining an included flowpath 92 at least equal in diameter to the conduit 68. The cap 76 in this embodiment is configured so that when substantially fully inserted sufficient pressure is exerted upon the packet either by direct contact or air cushion its rupture is caused. Thus, the proximal end wall of the packet which engages the flange 90 may be designed so as to be rupturable under the pressure conditions extant upon substantial cap insertion thereby releasing the auto-pressured Ibuprofen solution instead of abutting means, the internal diameter of the reservoir 64 may be necked down proximally so that closure of the cap 76 forces the packet into the smaller space, the resultant increased pressure causing rupture.

In the packet embodiments, flexible tip portions of the type illustrated in FIGS. 4 and 5 are recommended.

In FIG. 4, a flexible tip portion 94 is provided with a gate type valve 96 which is normally closed to prevent fluid flow between the conduit sections 98 and 98a, the latter terminating in the outlet aperture 100. The valve 96 is provided with a central horizontal slit to define equal upper and lower sections indicated at 102 and 104 in FIG. 4a. In closed position, the valve 96 provides a pressure resistant hermetic seal positionally stable against the pressure exerted by the contents of the reservoir 64. However, when the tip 94 is rotated as indicated by the directional arrow in FIG. 4a, as would be the case when the surface 106 of the tip 94 is pressed against a tooth, a flexure of the tip 94 causes the valve 96 to open to the position indicated by the valve sections 102 and 104 in FIG. 4a.

In FIG. 5, an inner surface 108 of the tip 100 is provided with normally closed slits 112, arranged substantially perpendicularly to the surface 108. In closed position, the slits provide a hermetic seal as described. However, when the surface 108 is pressed against a tooth, flexure of the tip 110 as indicated by the directional arrow of FIG. 5a causes the slits 112 to open providing the outlet aperture 112a for the pressurized Ibuprofen solution as indicated in FIG. 5a.

The tip portions as illustrated in FIGS. 5 and 5a are useful in the fluid (FIGS. 1-3) as well as packet embodiment (FIGS. 4 and 5). In the former case, the cap member is inserted and depressed to the maximum depth permitted by the resultant back pressure. This indicates maximum depth consistant with staple positioning of the cap. In use, the operator need only flex the tip portion in the manner described to initiate and sustain solution discharge, there being no need to depress the cap.

The tip portions herein may be hard rubber or similar polymeric material having equivalent resiliency and strength. The material selected should in any event be inert to the contained Ibuprofen solution. The outer surface of the tip should be nonirritating to the gums and tasteless. The tip may be interchangeable and may be attached to the device by simply inserting the proximal end of the handle member thereinto.

FIG. 6 is generally similar to FIG. 1 except that (a) conduit 20 enters the digital portion 68 of the handle member 12; (b) a valve 110 in the handle member 12 is in the form of a restrictor to control or halt flow through the conduit 20; and (c) reservoir 32 is in the form of a flask-like bottle having a pump 111 in its neck movable along the longitudinal axis of the flask-like bottom form of the reservoir 32.

The Ibuprofen solution may be in liquid or semisolid form.

In a further modification, valve means provided in the tip portion may be manipulated by control means suitably provided in the handle portion and mechanically connected thereto.

In a further preferred embodiment, the handle member is constructed of transparent material, e.g., inert film-forming synthetic organic polymer of types well known in the art enabling visual metering of dosage. Such handle may be graduated, bearing indicia enabling relatively precise assessment of dosage.

The following specific example is further illustrative of the nature of the present invention, but it is understood that the invention is not limited thereto. All amounts and proportions referred to herein are by weight unless otherwise indicated.

EXAMPLE

Fifteen adult squirrel monkeys are sedated and given a thorough prophylaxis following which the animals are evaluated for plaque and gingivitis at 36 maxillary and mandibular sites.

The monkeys are assigned to three balanced groups and randomly assigned to three treatment groups. Experimental periodontitis is induced in 2 monkeys from each group by applying silk ligatures around the bases (supragingivally) of the 1st and 2nd molars in one mandibular quadrant.

Contralateral teeth serve as controls. The experimental sites are initially evaluated for plaque and ginfivitis. In addition, a full microbiological assessment of the experimental sites is made. All of the animals are placed on a soft gingivitis-provoking diet.

Clinical and microbiological evaluations of the test sites are made at 3, 6, and 12 weeks. A histological evaluation of mandibles from monkeys which had sutures applied is performed at the study termination of 12 weeks.

All animals were treated once daily with the assigned treatments:
 Group I—Water control in the periodontal device of FIG. 6.
 Group II—1.0% Ibuprofen (aqueous solution) in the periodontal device of FIG. 6.
 Group III—1.0% Ibuprofen (aqueous solution) mouth rinse.

Ibuprofen is prepared as a 1% solution in distilled water (W/V) and adjusted to pH 7.7 by the addition of NaOH, $Na_2HPO_4.7H_2O$ and $KH_2PO_4$. The final concentration of phosphate buffer is approximately 0.0067M. The control solution contains the same concentration of phosphate buffer in distilled water. Approximately 5-6 cc of solutions are applied on all the dentition of the animals. The mouthrinse solution is delivered with polyethylene spray bottle. Solutions are given via the periodontal ddevice at a rate of 10 ml per minute (10 seconds/quadrant) in the gingival sulci.

The results of the study, are summarized in the Table below.

TABLE

Results of a histological evaluation of ligated sites for inflammation, expressed as a single score, the Mean

| Gingivitas Index Group | N | Mean Gingivitis Scores |
|---|---|---|
| Control in Perio Device | 4 | 1.75 |
| 1% Ibuprofen in Perio Device | 4 | 0.75 |
| 1% Ibuprofen Rinse | 4 | 1.87 |

N = Number of monkeys

The above results indicate that Ibuprofen solution administered with the periodontal device is clearly effective in reducing the histological indicators of inflammation particularly including inflammatory cell infiltration (as well as alveolar bone resorption) compared to either the control in the Perio Device or the 1% Ibuprofen rinse which exhibits no anti-inflamation antigingivitis effect compared to the control.

Similar antigingivitis effectiveness is obtained when the Ibuprofen solution employed in the periodontal device is the form of the sodium salt, aluminum salt, methyl ester and t-butyl ester.

It will be apparent to one skilled in the art that various modifications of the foregoing examples may be made thereto.

We claim:

1. A method for treating inflamed and swollen gingiva comprising inserting the tip portion of a periodontal gum device into inflamed and swollen gingival pocket and irrigating the affected areas with a sufficient amount of solution in said device to cause reduction of gingival inflammation and swelling; said device comprising an elongated member terminating proximally in a flexible tip portion provided with at least one aperture for discharge of the solution said solution containing 0.1–5% by weight of Ibuprofen, a pharmaceutically acceptable salt thereof or lower alkyl $C_{1-6}$ ester thereof, which is stored in a fluid reservoir in said device from which said solution is delivered to said aperture, said tip portion being configured to expedite probing contact with gingival sulcus and permit discharge of said solution into gingival sulcus.

2. The method claimed in claim 1 wherein said solution contains Ibuprofen, any of the potassium, sodium, calcium, magnesium or amine salt thereof or any of the methyl, ethyl, n-propyl, isopropyl, n-butyl, isobutyl, t-butyl, pentyl or hexyl esters thereof.

3. The method claimed in claim 2 wherein said solution contains Ibuprofen.

* * * * *